United States Patent [19]
Balli et al.

[11] 4,057,562
[45] Nov. 8, 1977

[54] CERTAIN NAPHTHOFURANS AND METHOD FOR THEIR MANUFACTURE

[75] Inventors: Heinz Balli, Riehen; Albert Egger, Allschwil, both of Switzerland

[73] Assignee: Ciba-Geigy Corporation, Ardsley, N.Y.

[21] Appl. No.: 673,240

[22] Filed: Apr. 2, 1976

Related U.S. Application Data

[62] Division of Ser. No. 524,850, Nov. 18, 1974, Pat. No. 3,974,180.

[30] Foreign Application Priority Data

Nov. 27, 1973 Switzerland .................. 16635/73

[51] Int. Cl.² ........................................... C07D 307/92
[52] U.S. Cl. ................................................. 260/346.71
[58] Field of Search ................................. 260/346.2 M

[56] References Cited

U.S. PATENT DOCUMENTS 2,894,003   7/1959   Long et al. ................. 260/346.2 M

*Primary Examiner*—Henry R. Jiles
*Assistant Examiner*—Bernard Dentz
*Attorney, Agent, or Firm*—Edward McC. Roberts; Prabodh I. Almaula

[57] ABSTRACT

The invention relates to specific naphthofurans which are useful as cryochromic substances e.g. for measuring the temperature, pH value or radiation field.

6 Claims, No Drawings

CERTAIN NAPHTHOFURANS AND METHOD FOR THEIR MANUFACTURE

This is a divisional of application Ser. No. 524,850, filed on Nov. 18, 1974 and now U.S. Pat. No. 3,974,180.

The invention relates to furans of the formula

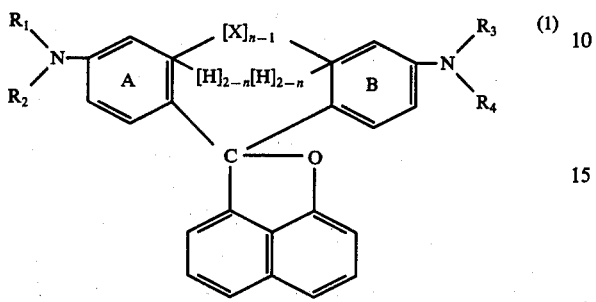

wherein $R_1$, $R_2$, $R_3$ and $R_4$ each denote alkyl with 1 to 4 carbon atoms or aryl, X denotes oxygen or sulphur and n denotes 1 or 2 and the rings A and/or B can optionally additionally be substituted by alkyl with 1 to 4 carbon atoms or halogen.

Examples of possible additional substituents of the rings A and B are alkyl radicals such as n-butyl, n-propyl, isopropyl, ethyl or above all methyl, or halogens such as iodine, bromine or above all chlorine.

X represents sulphur or preferably oxygen and can also be entirely absent.

$R_1$, $R_2$, $R_3$ and $R_4$ can have different meanings from one another or can, preferably, all be identical with one another.

Examples of possible R radicals are phenyl, n-butyl, n-propyl, isopropyl, ethyl or above all methyl.

Furans of outstanding interest are those of the formula

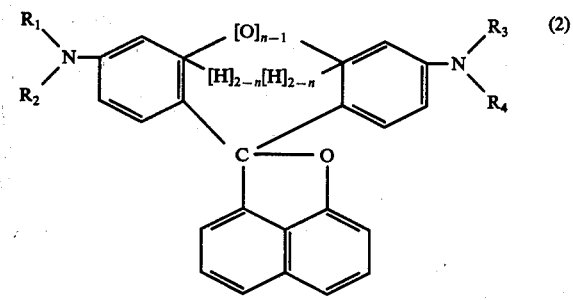

wherein $R_1$, $R_2$, $R_3$ and $R_4$, and n, have the indicated meaning.

Preferred furans correspond to the formula

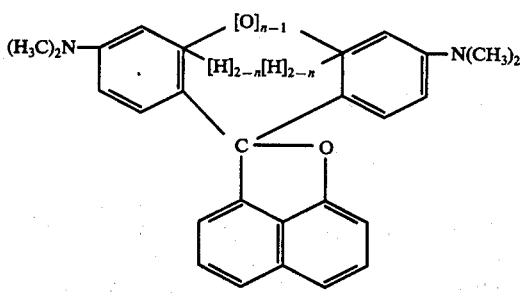

wherein n is 1 or 2.

A suitable method of manufacture of the furans of the formula (1) is to react a. a naphtholactone of the formula

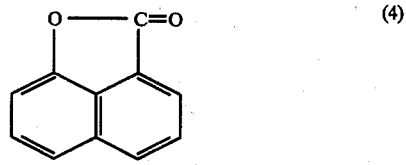

with b. at least one aniline of the formula

or

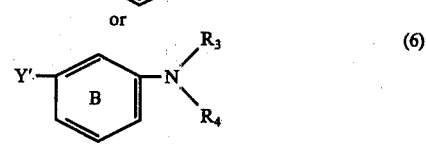

wherein Y and Y' each denote hydrogen, hydroxyl or thiol (SH) and A, B, $R_1$, $R_2$, $R_3$ and $R_4$ have the indicated meaning, at 150° to 220° C.

The preferred component (b) to use is an aniline of the formula

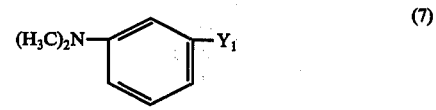

wherein $Y_1$ denotes hydrogen or hydroxyl.

The starting products employed for the manufacture of the furans of the formula (1) are preferably purified, and dried in a high vacuum, prior to the reaction. The naphtholactone can be purified by, for example, sublimation, the aminophenols can be purified by recrystallisation, for example from benzene-petroleum ether, and anilines can be purified by distillation.

The reaction of the components (a) and (b) is preferably carried out at 175° to 205° C. It is desirable to carry out the reaction in the presence of a catalyst such as a potentially acid salt, for example $MgCl_2$, $Zn(NO_3)_2$ or above all $ZnCl_2$.

Reactions of naphtholactone with an aniline are advantageously carried out with excess aniline, which at the same time serves as the solvent. Batches of 1 mol of naphtholactone with 2 to 4 mols of aniline have proved advantageous for this reaction. The addition of a solvent proper is not necessary but is possible.

Reactions of naphtholactone with an aminophenol are preferably carried out in the melt in the absence of solvents. Approximately stoichiometric amounts of the starting components, that is to say about 2 to 2.5 mols of aminophenol per mol of naphtholactone, have proved advantageous in this case.

If the desired furan of the formula (1) is to be obtained in a pure form, it is necessary to isolate it from the reaction mixture and purify it subsequently. A suitable method of separation is chromatography, especially column chromatography on aluminium oxide, which is carried out in a known manner with a solvent mixture, such as, for example, benzene-carbon tetrachloride or benzene-ethyldiisopropylamine or with a pure solvent, such as, for example, chloroform or benzene, as the flow medium.

The new compounds of the general formula (1) in solution exhibit the inverse property of "cryochromic" behaviour, related to the known phenomenon of "thermochromic properties". They are colourless in solution at temperatures of, for example, 60° to 100° C, and on cooling, for example to a temperature between 60° and −80° C, assume a colour which deepens with decreasing temperature. The process is reversible, that is to say on warming to 60° C the colour again disappears and the solution is colourless. The appearance of the colour depends on the pH value of the solution, that is to say the temperature at which a certain intensity of colour is reached through cooling can be varied by varying the pH value.

The phenomenon of "cryochromic properties" observed on the new compounds is probably attributable to the existence of an equilibrium between the structure I represented by the formula (1) and the form II which is opened at the oxygen atom of the furan radical. The opened form II contains an HO group on the naphthalene ring system, and is coloured, whilst the form I corresponding to the formula (1) is colourless.

The dependence of the concentration of the two equilibrium forms I and II on the temperature and the pH value is given, within a certain pH range, by $$\log c_{II}/c_I = a/T - b - p_H$$

wherein $c_I$ and $c_{II}$ are the concentration of the equilibrium forms I and II; T denotes the absolute temperature and $a$ and $b$ are constants of which the values can be determined empirically.

The colour can not only be caused to disappear by warming the solution to 60° C but can also be caused to disappear at low temperature by irradiation with light, especially light of short wavelengths, for example with ultraviolet radiation. As soon as the irradiation is discontinued, the original colour returns.

The rate at which the equilibrium is established or at which a disturbed equilibrium is re-established, that is to say the rate at which a certain colour intensity is obtained on cooling, or at which an existing colour is again caused to disappear by changing the pH value at constant temperature, or at which an existing colour disappears after irradiation or reappears after discontinuing the irradiation, depends essentially on the temperature and lies between less than one minute and about ten minutes.

The remarkable properties of the compounds of the formula (1) permit their use for measuring and testing processes in which changes in the temperature, the pH value or the radiation field play a role, or their utilisation for exerting a regulating action on the said parameters by means of the colourless ⇌ coloured equilibrium which has been described.

Examples which may be mentioned are their use to determine the pH distribution and especially the temperature distribution over a certain space, above all in large volumes, for investigating heat transfer and heat conduction processes and especially as "temperature warning colours", for example in conjunction with a light measuring device (photocell arrangement or the like), and for measuring and regulating temperatures. Further applications to be mentioned are their use in radiation warning instruments or in suitable devices for regulating incident radiation, for example in chemical or biological processes, as "chemical image converters" and possibly in devices for energy conversion, for example under extreme temperature conditions.

Further possible applications of the furans of the formula (1), resulting from their optical behaviour, are to be found in laser technology, where they can be used as optical switches, for example in the form of a solution which is introduced, in a cell, into the path of a beam of a gas, for the production of laser impulses.

For practical applications it is to be regarded as an advantage that the colour in the solution does not manifest itself abruptly on cooling but starts from completely colourless and increases continuously. In this way the cryochromic effect can be utilised, for example, for measuring and regulating the temperature over the entire range in question.

The cryochromic effect can also be utilised if the cryochromic substance, instead of being dissolved in a solvent, is converted to a semi-solid or solid form, provided it is ensured that the equilibrium which is dependent on the pH value becomes established correctly. Examples of possible semi-solid forms are solution or suspension in electrolyteconducting gelatinous masses (agar-agar) or the like. A solid form which may be mentioned is an embedded form in certain synthetic resins, for example of the type of the ion exchange resins.

In the examples which follow, percentages are percentages by weight.

EXAMPLE 1

100 mg of zinc chloride are added to a solution of 100 mg (0.6 mmol) of naphtholactone in 300 mg (2.5 mmols) of dimethylaniline at 200° C. As soon as all the naphtholactone has reacted (30 minutes), the reaction mixture is dissolved in ethanol and the solution is filtered and evaporated. After analysis by column chromatography (neutral aluminium oxide, activity IV, elution mixture 4 parts of benzene and 3 parts of carbon tetrachloride), 100 mg of light green product (40% of theory) are isolated. Crystallisation from ethanol gives colourless needles of melting point 184°-186° C.

The elementary analysis shows: $C_{27}H_{26}N_2O$ (394.5). Calculated: C, 82.2; H, 6.6; N, 7.1%; Found: C, 82.2; H, 6.6; N, 7.0%.

The 2,2-bis(p-N,N-dimethylaminophenyl)-2-H-naphtho[1,8-bc]furan thus obtained corresponds to the formula

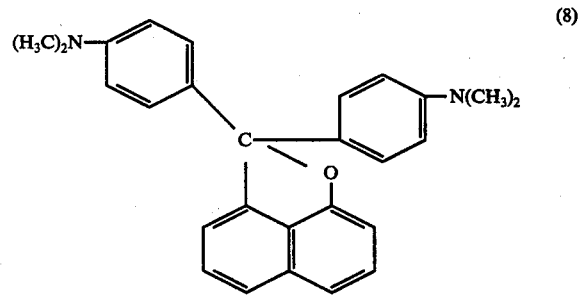

(8)

In 95% strength acetic acid, the furan of the formula (8) shows absorption maxima at 305, 395 and 613 nm.

An aqueous-ethanolic solution, containing sodium acetate, of the compound of the formula (8) is treated, if necessary, with a little 1 N sodium hydroxide solution, until any colour which may be present disappears. On cooling this solution to between 0° and −80° C, an intensive green colouration appears, which again disappears on warming the solution to room temperature.

EXAMPLE 2

0.35 g of zinc chloride is added to a melt of 0.80 g (5 mmols) of naphtholactone and 1.40 g of m-dimethylaminophenol (10 mmols) at 180° C.

After 30 minutes, the viscous melt is dissolved in dimethylformamide, the solution is covered with ether and the perchlorate of the furan is precipitated with an aqueous 10% strength sodium perchlorate solution (crude yield 2.6 g).

1.00 g of crude product is dissolved in acetone, the solution is evaporated with a ten-fold amount of aluminium oxide (neutral), and the product is filled into the top of a column (neutral aluminium oxide, activity IV). Elution is carried out with benzene containing 1% of ethyl-diisopropylamine. 400 mg (40% of theory) of the spiro-product are obtained. Three-fold crystallisation from ligroin (boiling point 100° to 140° C) containing 1% of ethyl-diisopropylamine gives colourless needles of melting point 241° to 242° C (300 mg, 30% of theory).

The elementary analysis shows: $C_{27}H_{24}N_2O_2$ (molecular weight 408.5). Calculated: C, 79.4; H, 5.9; N, 6.9%; Found: C, 79.1; H, 6.0; N, 6.9%.

The spiro-3,6-bis(dimethylamino)-xanthene-9,2-(2H)-naphtho[1,8-bc]-furan corresponds to the formula

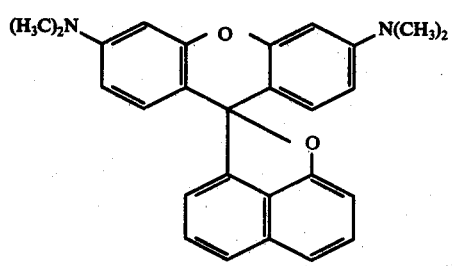
(9)

In 95% strength acetic acid, the furan of the formula (9) shows absorption maxima at 304, 348, 407 and 544 nm.

An aqueous-ethanolic solution saturated, at room temperature, with the compound of the formula (9and disodium hydrogen phosphate is treated, if necessary, with a little 1 N sodium hydroxide solution, until any colouration which may occur almost disappears. On cooling this solution to between 0° and −80° C, an intensive red colouration (λmax = 544 nm) occurs, which almost disappears on warming the solution to room temperature.

We claim:
1. A furan of the formula

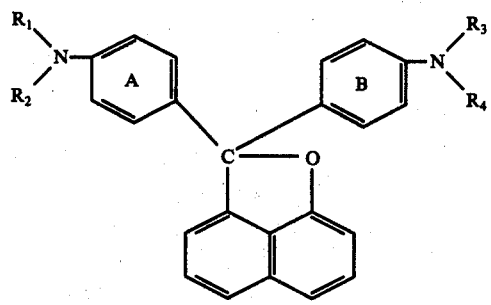

in which $R_1$, $R_2$, $R_3$ and $R_4$ are independently alkyl of 1 to 4 carbon atoms or phenyl;
and the phenyl rings A and B are independently unsubstituted or are substituted by alkyl of 1 to 4 carbon atoms or halo.

2. A furan according to claim 1, wherein $R_1$, $R_2$, $R_3$ and $R_4$ are alkyl of 1 to 4 carbon atoms and the phenyl rings A and B are unsubstituted.

3. The furan according to claim 1 of the formula

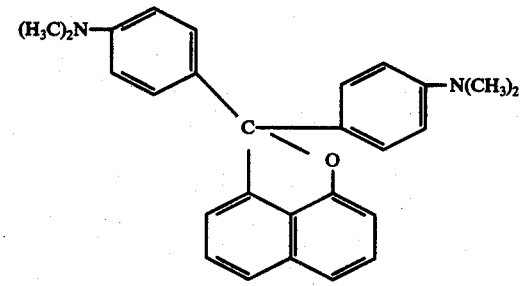

4. A process for the preparation of a furan of the formula

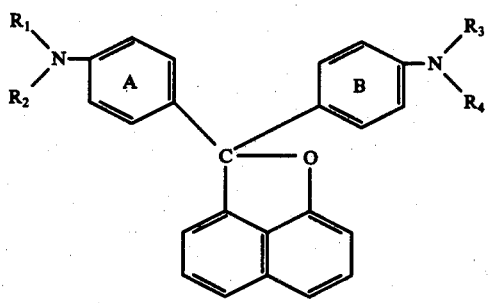

in which $R_1$, $R_2$, $R_3$ and $R_4$ are independently alkyl of 1 to 4 carbon atoms or phenyl;
and the phenyl rings A and B are independently unsubstituted or are substituted by alkyl of 1 to 4 carbon atoms or halo;
which comprises reacting
a. the naphtholactone of the formula

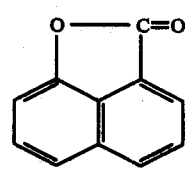

with
b. at least one aniline of the formula

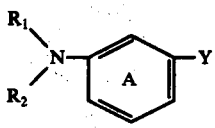
or
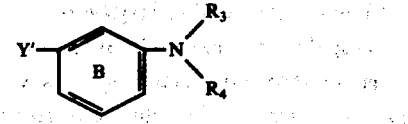
wherein
Y and Y' are each hydrogen, at 150° to 220° C.
5. Process according to claim 4, which comprises reacting at 175° to 205° C.
6. Process according to claim 4, which comprises reacting in the presence of a potentially acid salt.
* * * * *